United States Patent
Lho

(10) Patent No.: US 9,776,766 B1
(45) Date of Patent: Oct. 3, 2017

(54) CONTAINER FOR DENTAL APPLIANCES

(71) Applicant: Helen Lho, Beverly Hills, CA (US)

(72) Inventor: Helen Lho, Beverly Hills, CA (US)

( * ) Notice: Subject to any disclaimer, the term of this patent is extended or adjusted under 35 U.S.C. 154(b) by 0 days.

(21) Appl. No.: 15/470,515

(22) Filed: Mar. 27, 2017

Related U.S. Application Data

(63) Continuation of application No. 15/141,531, filed on Apr. 28, 2016, now Pat. No. 9,603,690.

(51) Int. Cl.
```
B65D 83/10     (2006.01)
B65D 25/10     (2006.01)
A45D 44/20     (2006.01)
B65D 43/16     (2006.01)
B65D 25/04     (2006.01)
A61C 19/02     (2006.01)
```

(52) U.S. Cl.
CPC ............. *B65D 25/10* (2013.01); *A45D 44/20* (2013.01); *A61C 19/02* (2013.01); *B65D 25/04* (2013.01); *B65D 43/163* (2013.01); *A45D 2200/05* (2013.01); *B65D 2251/105* (2013.01); *B65D 2543/00537* (2013.01)

(58) Field of Classification Search
CPC ........ A61C 19/02; A45D 44/20; A61B 50/30; A61B 2050/005; A61B 2050/3008
USPC ......... 206/63.5, 83, 368, 369, 438; 220/501, 220/529, 553, 554, 810
See application file for complete search history.

(56) References Cited

U.S. PATENT DOCUMENTS

| | | | |
|---|---|---|---|
| 2,375,645 A | | 5/1945 | Gordon |
| 2,620,919 A | * | 12/1952 | Passmore ........... B65D 81/1075 206/83 |
| 4,966,319 A | * | 10/1990 | Fleming ................ A45C 11/00 206/459.5 |
| 4,991,759 A | | 2/1991 | Scharf |
| 5,076,437 A | | 12/1991 | Schindler |
| 5,348,154 A | | 9/1994 | Jacobs et al. |
| 5,377,823 A | | 1/1995 | Steen et al. |
| 6,693,537 B2 | | 2/2004 | Frank |
| 6,705,333 B1 | | 3/2004 | Pourcho |
| 7,201,271 B1 | | 4/2007 | Saad |
| 2007/0138042 A1 | | 6/2007 | Wood |
| 2008/0283422 A1 | | 11/2008 | Jansheski |
| 2010/0181214 A1 | | 7/2010 | Brown |
| 2014/0263500 A1 | | 9/2014 | Brooks |
| 2016/0100924 A1 | | 4/2016 | Wilson et al. |

* cited by examiner

*Primary Examiner* — Luan K Bui
(74) *Attorney, Agent, or Firm* — Loeb & Loeb LLP

(57) ABSTRACT

A container for a dental appliance. The container includes a first compartment with at least one first wall, a first enclosing portion, and a separation plate. The first compartment includes a length, a width, and a height to accept a first dental appliance and indicated by a first indicator. The container includes a second compartment defined by at least one second wall, a second enclosing portion, and the separation plate. The second compartment includes a second length, second width and second height to accept a second dental appliance and indicated by a second indicator. The container includes a moveable and closeable door which opens to permit access to at least one of the first compartment and the second compartment. The dental appliance in the first compartment is separate from the dental appliance in the second compartment by the separation plate, and the container comprises ports to allow circulation.

20 Claims, 8 Drawing Sheets

CONTAINER FOR DENTAL APPLIANCES

CROSS-REFERENCE TO RELATED APPLICATIONS

This application is a continuation of and claims priority to U.S. patent application Ser. No. 15/141,531, filed Apr. 28, 2016, entitled, "CONTAINER FOR DENTAL APPLIANCES." The entire contents of the aforementioned application is expressly incorporated by reference herein.

BACKGROUND

For many people who use various types of dental appliances and devices, such as retainers, dentures, etc., it may be necessary to frequently store the appliances between uses or for transport. Existing options for storage of such dental appliances tend to be quite rudimentary, without any means of keeping devices designed for top teeth and bottom teeth separate. Further, existing containers provide no indication as to their contents in a readily ascertainable manner.

An improved container for more convenient and practical storage of dental appliances is needed.

SUMMARY

In an embodiment, the disclosure describes a container for a dental appliance. The container includes a first compartment defined by at least one first wall, a first enclosing portion, and a separation plate. The first compartment includes a length, a width and a height to accept a first dental appliance and indicated by a first indicator. The container includes a second compartment defined by at least one second wall, a second enclosing portion, and the separation plate. The second compartment includes a second length, second width and second height to accept a second dental appliance and indicated by a second indicator. The container also includes a moveable and closeable door which opens to permit access to at least one of the first compartment and the second compartment. The first dental appliance in the first compartment is separate from the second dental appliance in the second compartment by the separation plate, and the container comprises a plurality of ports to allow circulation.

BRIEF DESCRIPTION OF THE DRAWINGS

The invention may be better understood by reference to the detailed description when considered in connection with the accompanying drawings. The components in the figures are not necessarily to scale, emphasis instead being placed upon illustrating the principles of the invention. In the figures, like reference numerals designate corresponding parts throughout the different views.

Figure 1:
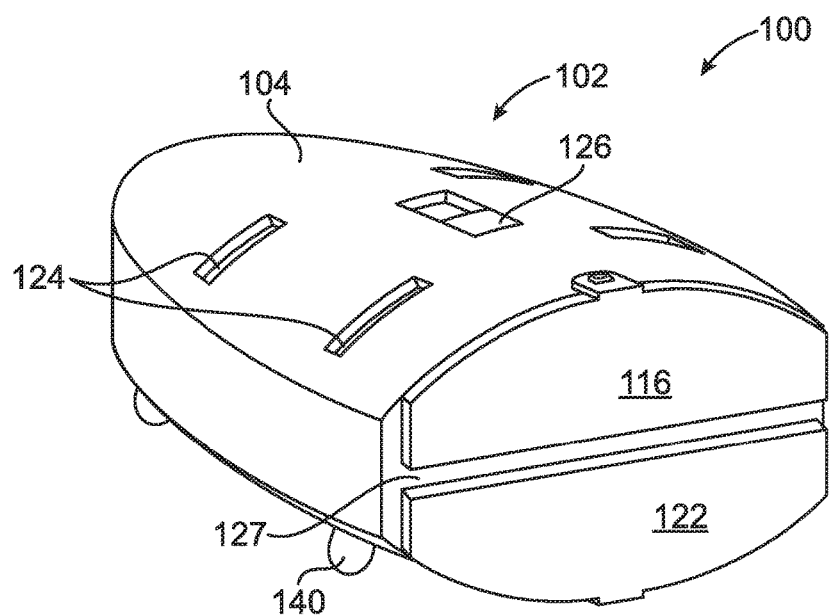
FIG. 1 is a perspective view of one exemplary embodiment of a container for dental appliances in a closed position in accordance with the disclosure.

Persons of ordinary skill in the art will appreciate that elements in the figures are illustrated for simplicity and clarity so not all connections and options have been shown to avoid obscuring the inventive aspects. For example, common but well-understood elements that are useful or necessary in a commercially feasible embodiment are not often depicted in order to facilitate a less obstructed view of these various embodiments of the present disclosure. It will be further appreciated that certain actions and/or steps may be described or depicted in a particular order of occurrence while those skilled in the art will understand that such specificity with respect to sequence is not actually required. It will also be understood that the terms and expressions used herein are to be defined with respect to their corresponding respective areas of inquiry and study except where specific meanings have otherwise been set forth herein.

DETAILED DESCRIPTION

The present invention now will be described more fully hereinafter with reference to the accompanying drawings, which form a part hereof, and which show, by way of illustration, specific exemplary embodiments by which the invention may be practiced. This invention may, however, be embodied in many different forms and should not be construed as limited to the embodiments set forth herein; rather, these embodiments are provided so that this disclosure will be thorough and complete, and will fully convey the scope of the invention to those skilled in the art. Among other things, the present invention may be embodied as methods or devices. Accordingly, the present invention may take the form of an entirely hardware embodiment, an entirely software embodiment or an embodiment combining software and hardware aspects. The following detailed description is, therefore, not to be taken in a limiting sense.

Throughout the specification and claims, the following terms take the meanings explicitly associated herein, unless the context clearly dictates otherwise. The phrase "in one embodiment" as used herein does not necessarily refer to the same embodiment, although it may. Furthermore, the phrase "in another embodiment" as used herein does not necessarily refer to a different embodiment, although it may. Thus, as described below, various embodiments of the invention may be readily combined, without departing from the scope or spirit of the invention.

In addition, as used herein, the term "or" is an inclusive "or" operator, and is equivalent to the term "and/or," unless the context clearly dictates otherwise. The term "based on" is not exclusive and allows for being based on additional factors not described, unless the context clearly dictates otherwise. In addition, throughout the specification, the meaning of "a," "an," and "the" include plural references. The meaning of "in" includes "in" and includes plural references. The meaning of "in" includes "in" and "on."

The disclosure is directed to embodiments of a container for holding dental appliances. The container generally includes multiple compartments or areas for holding dental appliances or portions of dental appliances when not in use or when being stored for later use. In some embodiments, the container provides separation of two or more dental appliances in two or more compartments so as to allow for a user to easily discern between the different appliances when in a stored position. The container itself may include indicators of whether dental appliances are occupying each individual compartment, and may provide ready indication of which portion of a dental appliance or appliances is occupying each container. In general, the embodiments of the container described and shown herein allow for improved storage, access, and organization of dental appliances.

Figure 2:
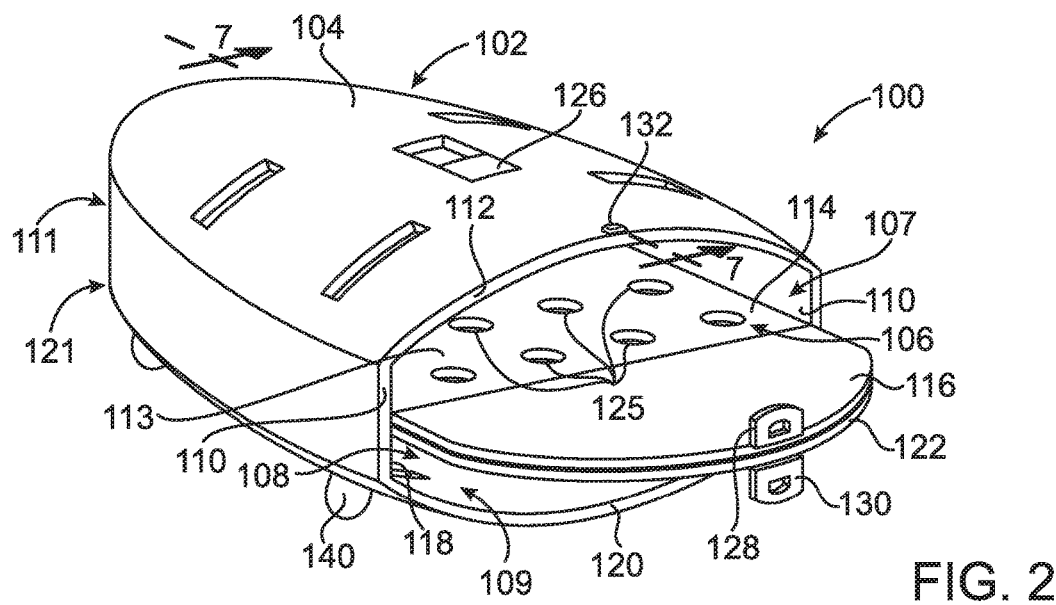
FIG. 2 is a perspective view of the container of FIG. 1 in an open position.
Figure 3:
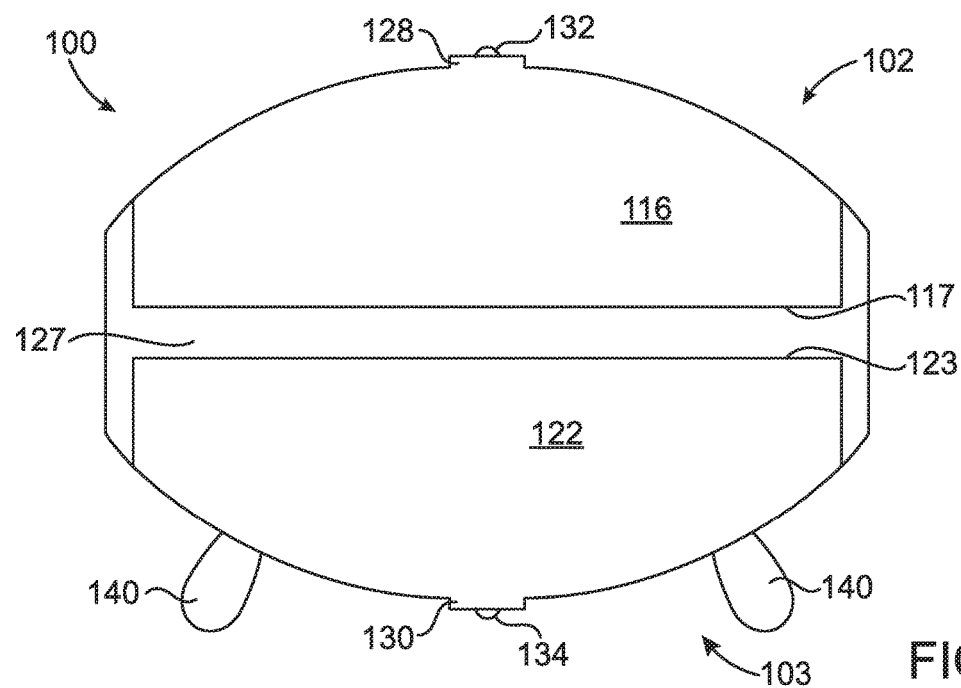
FIG. 3 is a front view of the container of FIG. 1 in the closed position.
Figure 7:
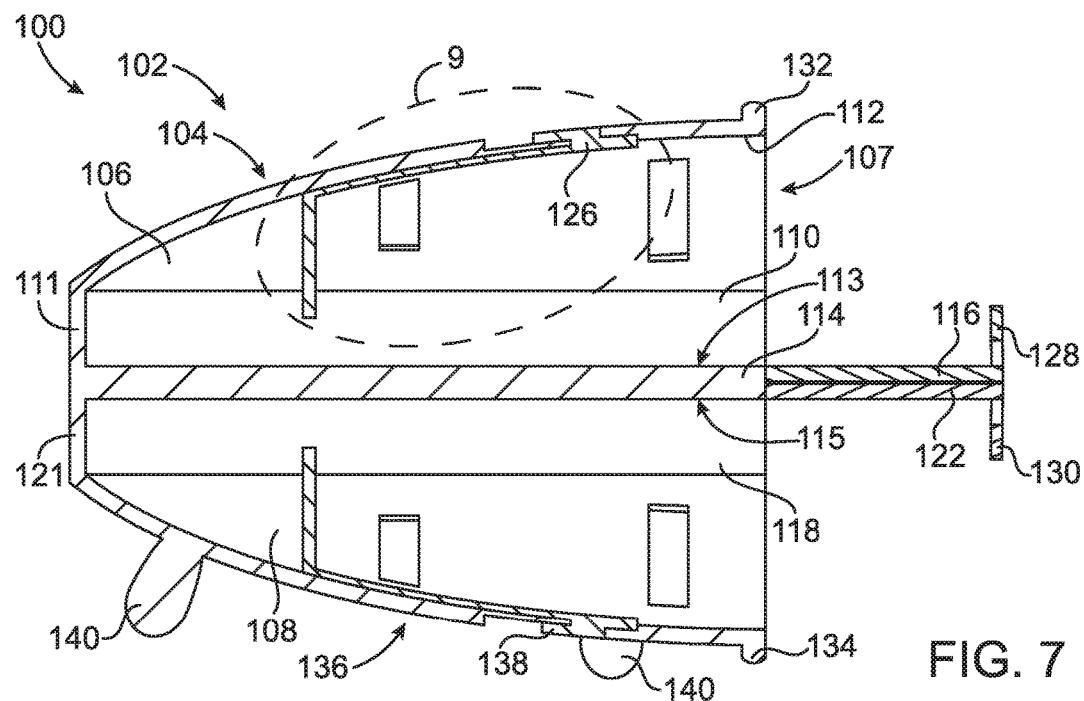
FIG. 7 is a left side sectional view of the container of FIG. 1 including a mechanical sensing device in the open position.

FIGS. 1-7 illustrate multiple views of an embodiment of a dental appliance container 100 in a closed position (FIGS. 1, 3, 4, and 5) and an open position (FIGS. 2 and 7). As best shown in FIG. 2, a first compartment or area 106 and a second compartment or area 108 for holding dental appliances or portions of dental appliances are formed within the container 100. The first compartment 106 is defined in the container 100 by at least one first wall 110, a first enclosing portion 112, and a separation plate 114. The first wall 110 at least partially surrounds the first compartment 106. In the illustrated embodiment, the first wall 110 is substantially C-shaped, providing a substantially vertical, curved wall around the first compartment 106 while allowing for a first access opening 107. A first side 113 of the separation plate 114 may define a floor of the first compartment 106 and separate the first compartment from the second compartment 108. In some embodiments, the separation plate 114 may be integral with the first wall or, in other embodiments, may be separate from the first wall and may be removable from the container. In some embodiments, the separation plate 114 may be moved between multiple positions to provide larger or smaller first and second compartments depending on the position of the separation plate. The first enclosing portion 112 may be connected to an upper edge of the first wall 110 and be disposed opposite the separation plate 114, defining an upper limit of the first compartment 106. In some embodiments, the first enclosing portion 112 may be integral with the first wall 110. A height of the first compartment 106 may be defined between the first side 113 of the separation plate 114 and the first enclosing portion 112, and a width of the first compartment may be defined across the first access opening 107 between opposite ends of the first wall 110. A length of the first compartment 106 may be defined between the first access opening 107 and a rear portion 111 of the first wall 110.

The second compartment or area 108 may be defined within the container 100 by at least one second wall 118, a second enclosing portion 120, and the separation plate 114. The second wall 118 may at least partially surround the second compartment 108. In the illustrated embodiment, the second wall 118 is substantially C-shaped, providing a substantially vertical, curved wall around the second compartment 108 while allowing for a second access opening 109. The second compartment 108 may be formed within the container 100 on the opposite side of the separation plate 114, such that a second side 115 of the separation plate may define a ceiling of the second compartment. In some embodiments, the separation plate 114 may have plate ventilation ports 125 formed between the first and second sides 113, 115 of the separation plate. In such embodiments, the plate ventilation ports 125 may provide fluid communication between the first compartment 106 and the second compartment 108 so as to facilitate air flow. In some embodiments, the second wall 118 and the first wall 110 may be integral with one another and/or the separation plate 114. In other embodiments, the first and second walls 110, 118 may be separate and connected to one another by any suitable fastener or adhesive. The second enclosing portion 120 may be connected to a lower edge of the second wall 118 and be disposed opposite the separation plate 114, defining a lower limit of the second compartment 108. In some embodiments, the second enclosing portion 120 may be integral with the second wall 118. A height of the second compartment 108 may be defined between the second side 115 of the separation plate 114 and the second enclosing portion 120, and a width of the first compartment may be defined across the second access opening 109 between opposite ends of the second wall 118. A length of the second compartment 108 may be defined between the second access opening 109 and a rear portion 121 of the second wall 118.

Figure 4:
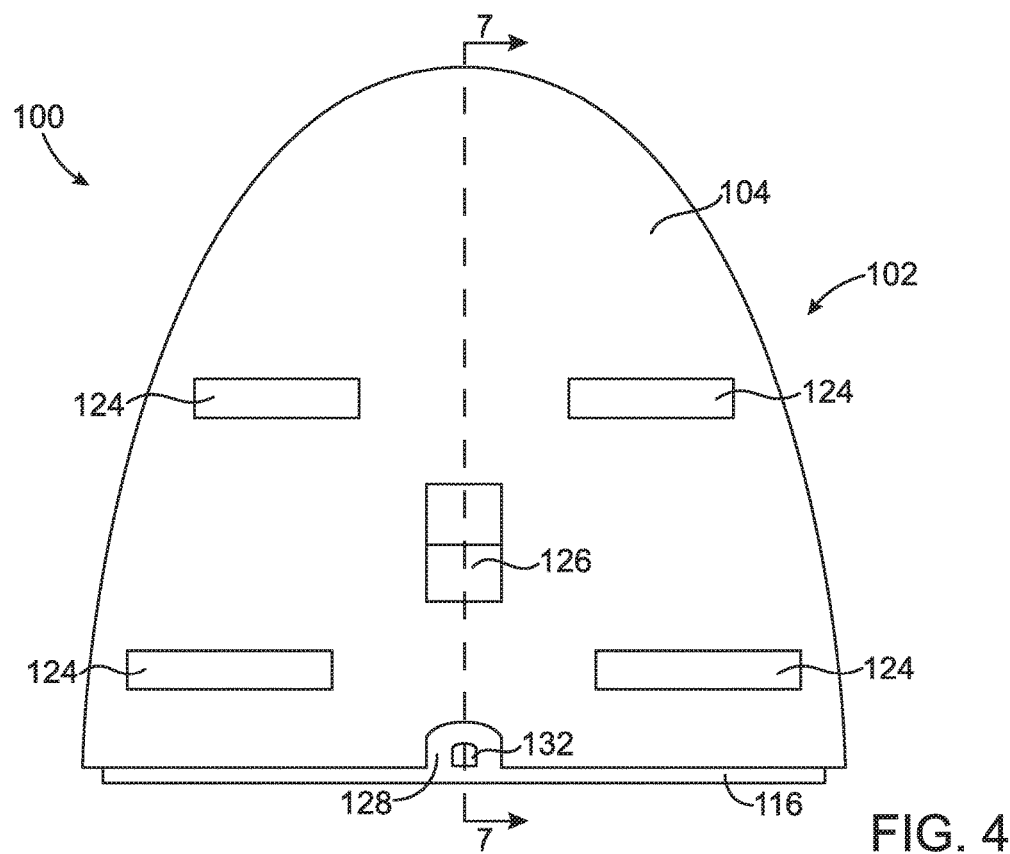
FIG. 4 is a top view of the container of FIG. 1 in the closed position.
Figure 5:
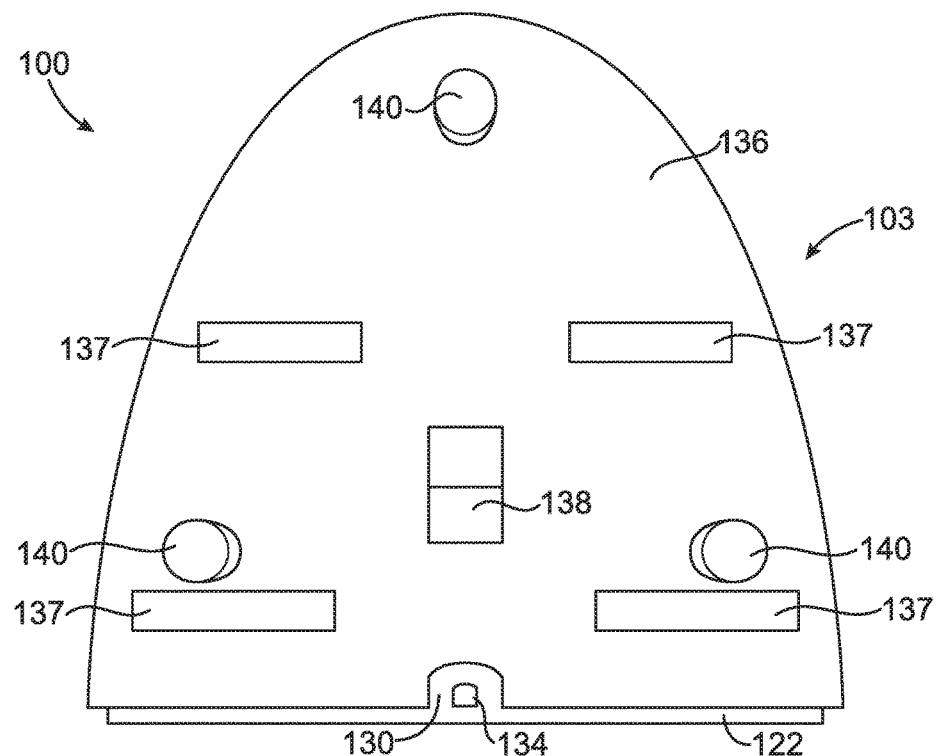
FIG. 5 is a bottom view of the container of FIG. 1 in the closed position.
Figure 6:
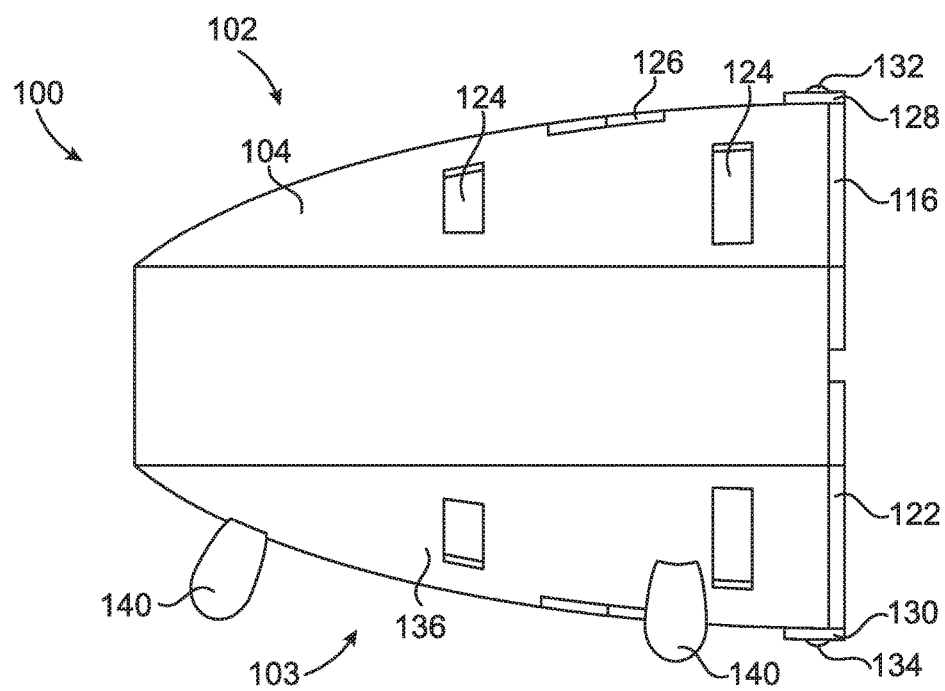
FIG. 6 is a left side view of the container of FIG. 1 in the closed position.

The first access opening 107 and the second access opening 109 may be selectably occluded by at least one moveable and closeable door. In the embodiment shown in FIGS. 1 and 2, a first door 116 may move between a closed and open position to permit access to the first compartment 106 via the first access opening 107, and a second door 122 may move between a closed position and an open position to permit access to the second compartment 108 via the second access opening 109. In some embodiments, however, such as the embodiment illustrated in FIG. 11, both the first and second access openings 107, 109 may be selectably occluded by a dual door 302 in the container 300. In the embodiment of the container 100 shown in FIGS. 1-7, the first and second doors 116, 122 move between the open and closed positions by pivoting about a first hinged end 117 on the first door and a second hinged end 123 on the second door. In some embodiments, such as the embodiment shown in FIGS. 1 and 2, the first and second doors 116, 122 may be pivotally connected to an exposed edge 127 of the separation plate 114 along the first and second hinged ends 117, 123, respectively. The first and second hinged ends 117, 123 may form a pivotal connection with the separation plate 114 by any suitable hinging mechanism, such as a molded hinge connected to both the doors and the separation plate, or separate hinges that connect the doors to the plate. In some embodiments, it is contemplated that the first and second doors 116, 122 may be instead or alternatively be pivotally connected to the first and second enclosing portions 112, 120, respectively. Additionally, the first and second doors 116,122 may include closure mechanisms, for example, first and second latches 128, 130, respectively, disposed on the first and second doors opposite the hinged ends 117, 123. As best shown in FIG. 4, the first latch 128 may engage with a first retention knob 132 to retain the first door 116 in a closed position occluding the first access opening 107. Similarly, as best shown in FIG. 5, the second latch 130 may engage with a second retention knob 134 to retain the second door 122 in a closed position occluding the second access opening 109. Those skilled in the art, however, will recognize that a variety closure mechanisms may be employed to suitably retain the first and second doors 116, 122 in the closed position, all of which are also contemplated herein.

FIGS. 3-6 show front, top, bottom, and side views of the container 100, respectively. The illustrated container 100 has a top portion 102 and a bottom portion 103. The top portion 102 includes a generally convex top surface 104 forming an outer surface of the first enclosing portion 112. Although the top surface 104 is shown as generally convex, other curved or rounded surfaces are contemplated as well. As best shown in FIG. 4, the top surface 104 may include at least one ventilation port 124 or set of ventilation ports, a first appliance indicator 126, and a first retention knob 132. The ventilation ports 124 are formed into the first enclosing portion 112 so as to provide fluid communication between the top surface 104 and the first compartment 106. Providing such fluid communication into the first compartment 106 through the ventilation ports 124 allows for air circulation throughout the interior of the container 100, which may aid in drying a dental appliance stored therein. Although the container 100 illustrated herein includes four ventilation ports 124 in the top surface 104, it is contemplated that other numbers of ventilation ports may be used in other embodiments.

The first appliance indicator 126 is configured to move between a position indicating that a dental appliance is within the first compartment 106 and a position indicating that no dental appliance is present within the first compartment. The first appliance indicator is described in greater detail below with reference to FIGS. 7-10. The first retention knob 132 may be formed integral with the top surface 104 and engage with the first latch 128 to retain the first door 116 in a closed position occluding the first access opening 107.

The bottom portion 103 of the container 100, as best shown in FIG. 5, may include a bottom surface 136 that may form an outer surface of the second enclosing portion 120. Although the bottom surface 136 is shown as being generally convex, it is contemplated herein that the bottom surface could have different configurations, such as concave, flat, or rounded. The bottom surface 136 may include at least one ventilation port 137 or set of ventilation ports, a second appliance indicator 138, and a second retention knob 134. The ventilation ports 137 are formed into the second enclosing portion 120 so as to provide fluid communication between the bottom surface 136 and the second compartment 108. Similar to the ventilation ports 125 in the top surface 104, providing such fluid communication into the second compartment 108 through the ventilation ports 137 allows for air circulation throughout the interior of the container 100, which may aid in drying dental appliances stored therein. Although the container 100 illustrated herein includes four ventilation ports 137 in the bottom surface 136, it is contemplated that other numbers of ventilation ports may be used in other embodiments.

The second appliance indicator 126 is configured to move between a position indicating that a dental appliance is within the second compartment 108 and a position indicating that no dental appliance is present within the second compartment. The appliance indicators are described in greater detail below with reference to FIGS. 7-10. The second retention knob 134 may be formed integral with the bottom surface 136 and engage with the second latch 130 to retain the second door 122 in a closed position occluding the first access opening 107. Although the first and second doors 116, 122 are described herein as being pivotally connected to the separation plate 114 or other parts of the container 100 with a latch system, other connecting systems for movably connecting the first and second doors to the container and retaining them in closed position are also contemplated herein.

The bottom portion 103 may also include at least one foot 140 that may engage with a surface to stabilize the container 100 in an upright position, where the first compartment 106 is positioned above the second compartment 108. Although the figures show an embodiment that includes three feet 140, other numbers of feet that would suitably support the container 100 in an upright position when resting on the bottom portion 103 are contemplated herein.

The features of the container 100 are such that it may accept dental appliances within its compartments 106, 108, and stably rest in an upright position upon the bottom portion 103. If, however, the container 100 is set down on the convex or rounded top surface 104, the curvature of the top surface will may prevent the container from resting in a primarily horizontal position. An advantage of this configuration is that the container 100 will only readily rest in a primarily horizontal position when the bottom surface 136 is facing downward. As a result, the user will always know that the first compartment 106 is above the second compartment 108 and, therefore, always know immediately which dental appliance belongs or is present within which container.

Figure 9:
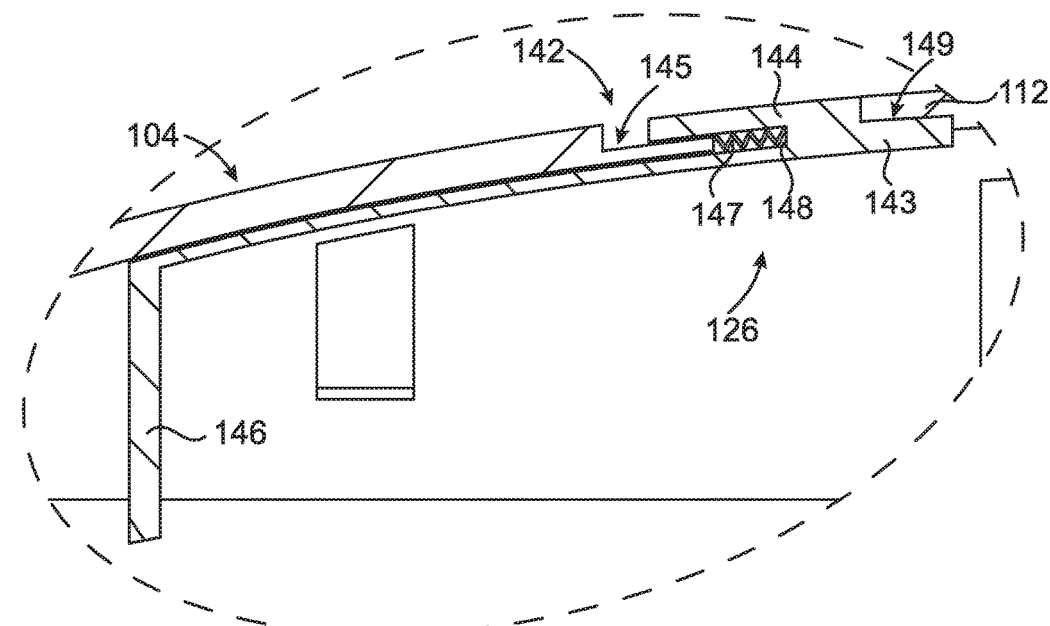
FIG. 9 is an enlarged left side sectional view of an indicator system of the container of FIG. 1 in an empty indicator position.
Figure 10:
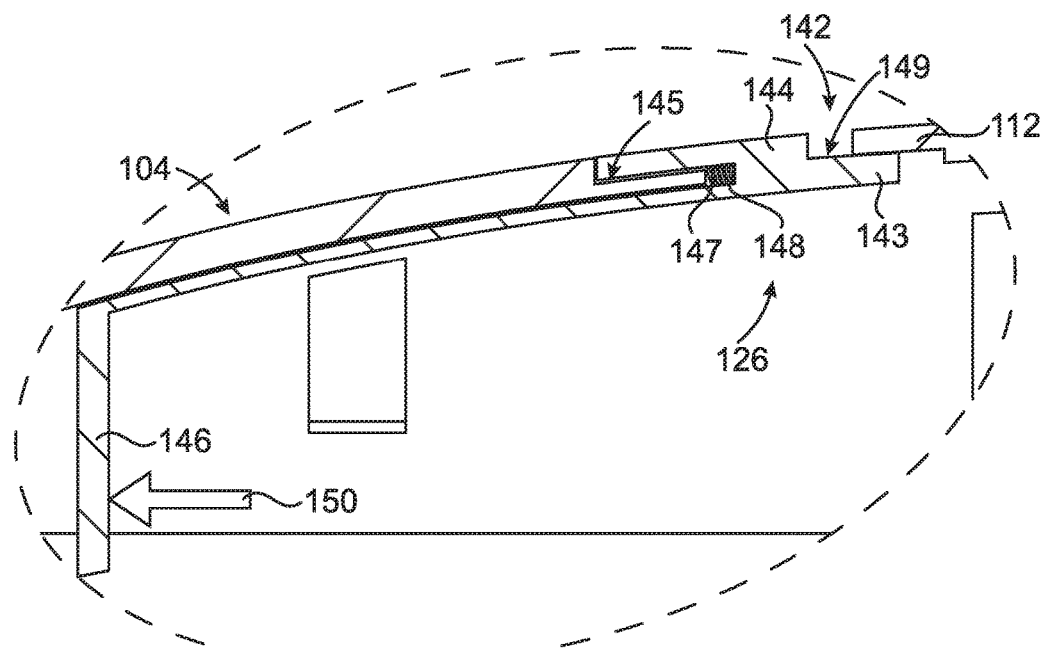
FIG. 10 is an enlarged left side sectional view of the indicator system of FIG. 9 in an occupied indicator position.

FIG. 7 shows a side cross-sectional view of the container 100 as indicated in FIG. 4. In FIG. 7, the both the first and second doors 116, 122 are in the open position, providing access to the first and second compartment 106, 108, respectively. The container 100 in FIG. 7 also includes embodiments of the first and second appliance indicator systems 126, 138. The first and second appliance indicator systems 126, 138 operate mechanically by causing an indicator window 142, 152, respectively, to show first or second indicator surfaces depending on whether a dental appliance is present within the first and second compartments 106, 108. FIGS. 9 and 10 are zoomed-in drawings of an embodiment of the first appliance indicator 126. It should be understood, however, that the second appliance indicator 138, though not shown in complete detail, may include similar features and operate in a similar manner. The first appliance indicator system 126 may include a first indicator window 142 formed into the top surface 104 of the container 100. A first indicator switch 143 may be movably and slidably disposed within the first indicator window 142 such that a sliding portion 144 of the first indicator switch 143 may slide between an occupied position and an empty position within the first indicator window. When in the empty position, as shown in FIG. 9, the sliding portion 144 of the first indicator switch 143 allows for exposure of an empty indicator surface 145. Additionally, in the empty position, an occupied indicator surface 149 is covered by a portion of the first enclosing portion 112.

The first appliance indicator system 126 may also include a first sensing device, such as a wand 146, connected to the first indicator switch 143 that may extends into the first compartment 106, and a first biasing mechanism 147, such as a spring, disposed between the first enclosing portion 112 and the first indicator switch. When no dental appliance is present within the first compartment 106, the first biasing mechanism 147 may extend to exerts a biasing force against a first stop surface 148 of the first indicator switch 143 that holds the sliding portion 144 in the empty position, as shown in FIG. 9. When, such as in FIG. 10, a force 150 that is greater than the biasing force is applied against the wand 146, the first biasing mechanism 147 may compress, allowing the sliding portion 144 to slide into the occupied position. The force 150 may be provided by an item place into the first compartment 106, such as a first dental appliance. In the occupied position, the first indicator switch 143 is in a position such that the occupied indicator surface 149 is exposed and visible through the first indicator window 142. Additionally, in some embodiments, the wand 146 may control the dental appliance from excessive movement within the first compartment 106. When the dental appliance is removed, the first biasing mechanism 147 may apply a biasing force against the first stop surface and move the sliding portion 144 back to the empty position.

Thus, a user may ascertain whether a dental appliance or other item is present and secured within the first compartment 106 without opening the first door 116 by looking at whether the empty indicator surface 145 or the occupied indicator surface 149 is visible through the first indicator window 142. In some embodiments, it is contemplated that the empty and occupied indicator surfaces 145, 149 may include differing coloring, patterns, or words printed upon the respective surfaces to aid the user in determining which position the first indicator switch 126 is in. Although a detailed description of the second indicator system 138 is not included herein, a person skilled in the art would understand that the second indicator system may operate in a substantially similar manner as the first indicator system 126 in providing a visual indication as to whether a second dental appliance is present within the second compartment 108. In some embodiments, however, a first indication provided by the first indicator system 126 may be different than a second indication provided by the second indication system 138.

Figure 8:
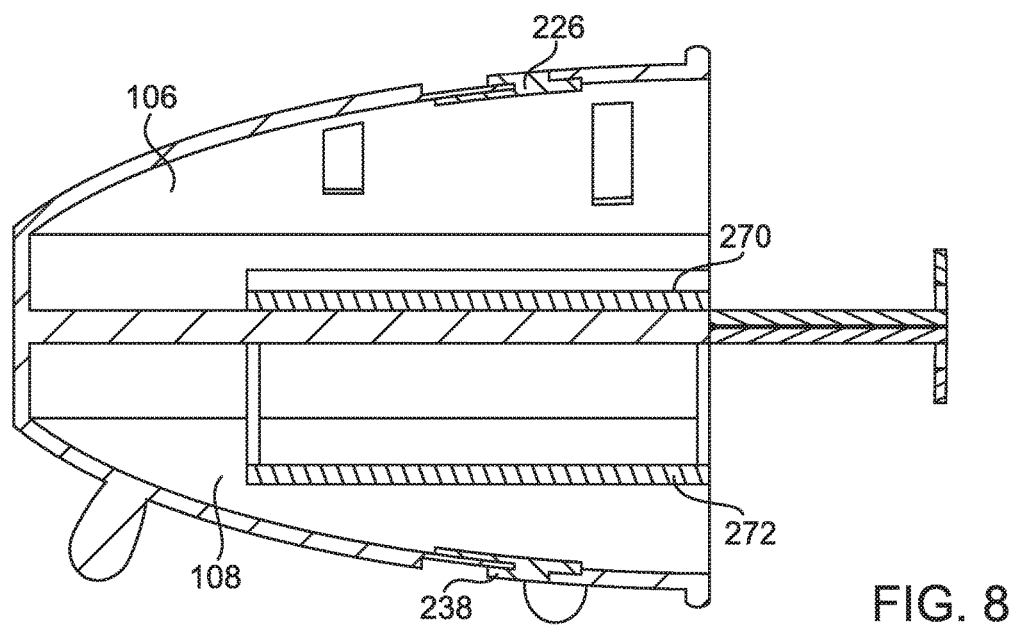
FIG. 8 is a left side sectional view of the container of FIG. 1 including an electronic sensing device in the open position.

FIG. 8 shows the container 100 equipped with another type of sensor for use in first and second indicator systems 226, 238 embodiment; specifically, indicator systems that include first and second electronic sensors 270, 272, respectively. In such embodiments, the first electronic sensor 270 may sense the presence of a first dental appliance within the first compartment 106 and cause the first indicator 126 to move from a position indicating that the first compartment is empty to a position indicating that the first compartment is occupied. Similarly, the second electronic sensor 272 may sense the presence of a second dental appliance within the second compartment 108 and cause the second indicator 238 to move from a position indicating that the second compartment is empty to a position indicating that the second compartment is occupied. In some embodiments, the first and second electronic sensors 270, 272 may be trays or platforms that incorporate pressure sensors, proximity sensors, radio frequency identification (RFID), or other sensing means suitable to detect the presence of a dental appliance within the first and/or second compartments 106, 108. Once the presence is detected by the sensors 270, 272 a signal may be sent to the first or second indicators 226, 238 in by any suitable mechanism, either wired or wirelessly transmitted. The first or second indicators 226, 238 may be moved from the empty to occupied indicator position using an electronically activated mechanism, such as a solenoid.

It should be understood that the indicator systems shown and described with respect to FIGS. 7-10 are but examples of systems for indicating whether a dental appliance is present within the first and/or second compartments 106, 108. Embodiments for other suitable indication systems are also contemplated herein.

Figure 11:
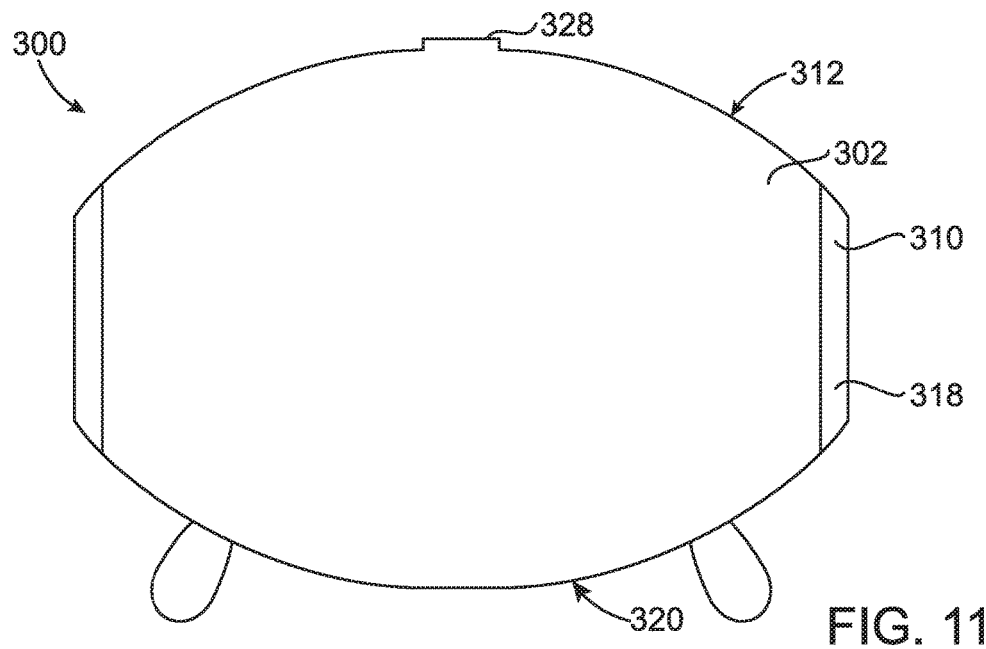
FIG. 11 is a front view of another embodiment of a container for dental appliances in accordance with the disclosure.

FIG. 11 includes an alternative embodiment of a container 300 similar to container 100, but with a single door 302 that is movable and closeable to provide or prevent access to first and second compartments. The single door 302 may be pivotally connected to the second enclosing portion 320 and may include a latch 328 to retain the door in a closed position. It is also contemplated that the single door may, alternatively, be pivotally connected to first and second walls 310, 318 of the container 300, or be pivotally connected to the first enclosing portion 312.

In some embodiments, the single door 302 may open in a clamshell type fashion to allow easy access to the first compartment 106 and second compartment 108 and the separation plate 114, which also may be pivotally connected to first and second walls 310, 318 of the container 300, or be pivotally connected to the first enclosing portion 312 or may rest on a ledge in either the first compartment 106 or second compartment 108. In some additional embodiments, the single door 302 may be integral with the first enclosing portion 112 and may also include the either the first wall 310. Further, in another embodiment, the single door 302 may be integral with the second enclosing portion 120 and may also include the second wall 318. Other suitable mechanisms for movably connecting the single door 302 to the container 300 are also contemplated herein.

Figure 12:
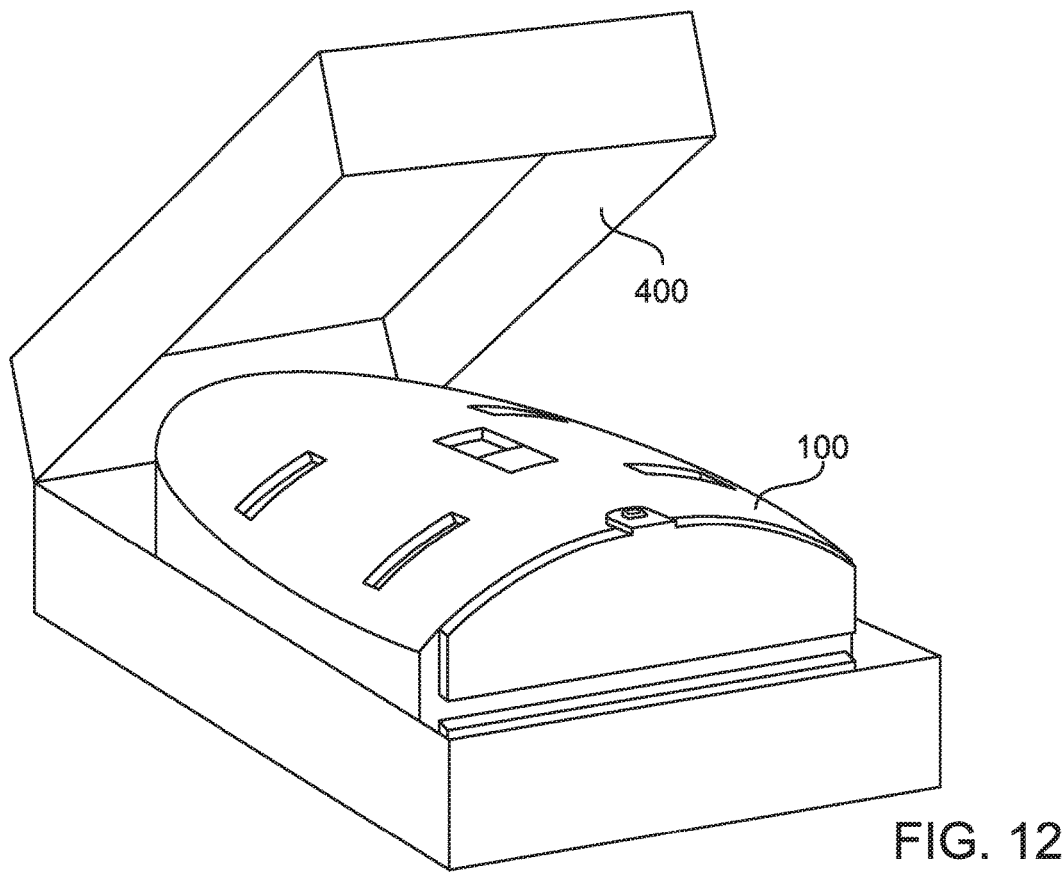
FIG. 12 is a perspective view of the container of FIG. 1 enclosed within a surrounding container.

FIG. 12 includes a surrounding container 400 that may enclose the container 100. The surrounding container 400 may retain the container 100 for storage or for transportation. In some embodiments, the surrounding container 400 does not have circulation openings.

Figure 13:
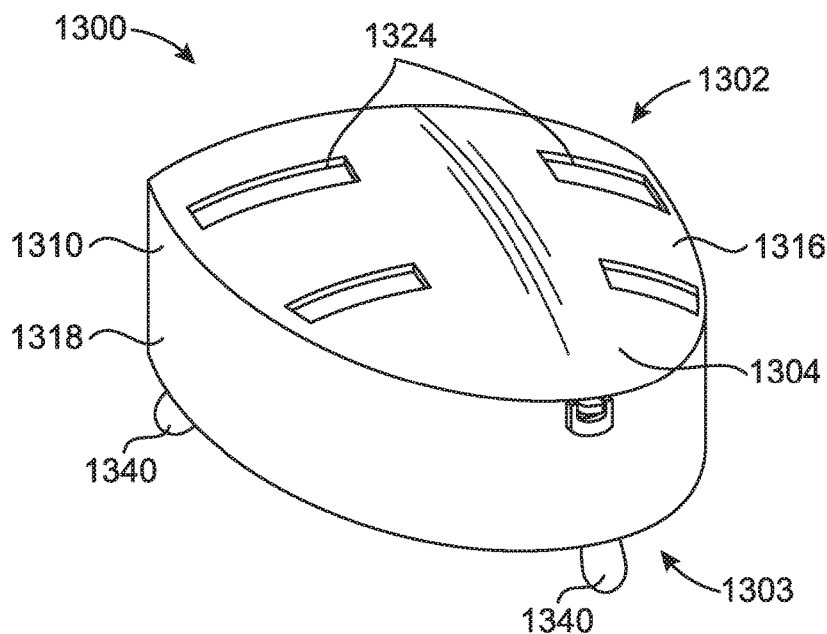
FIG. 13 is a perspective view of another embodiment of a container for dental appliances in accordance with the disclosure, shown in a closed position.
Figure 14:
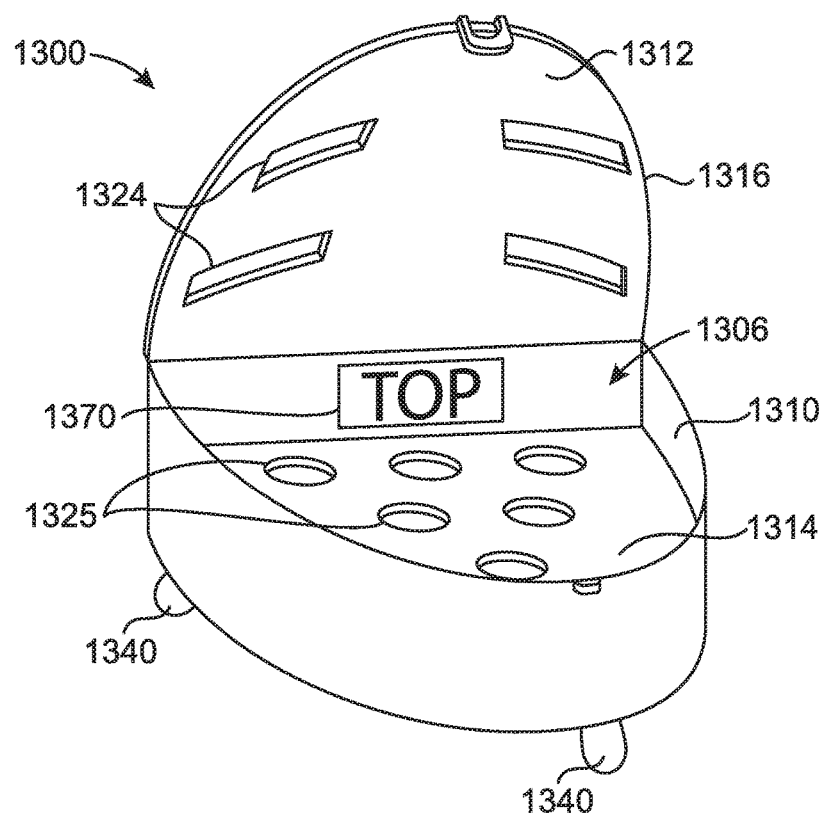
FIG. 14 is a perspective view of the container for dental appliances of FIG. 13 shown in an open position.
Figure 15:
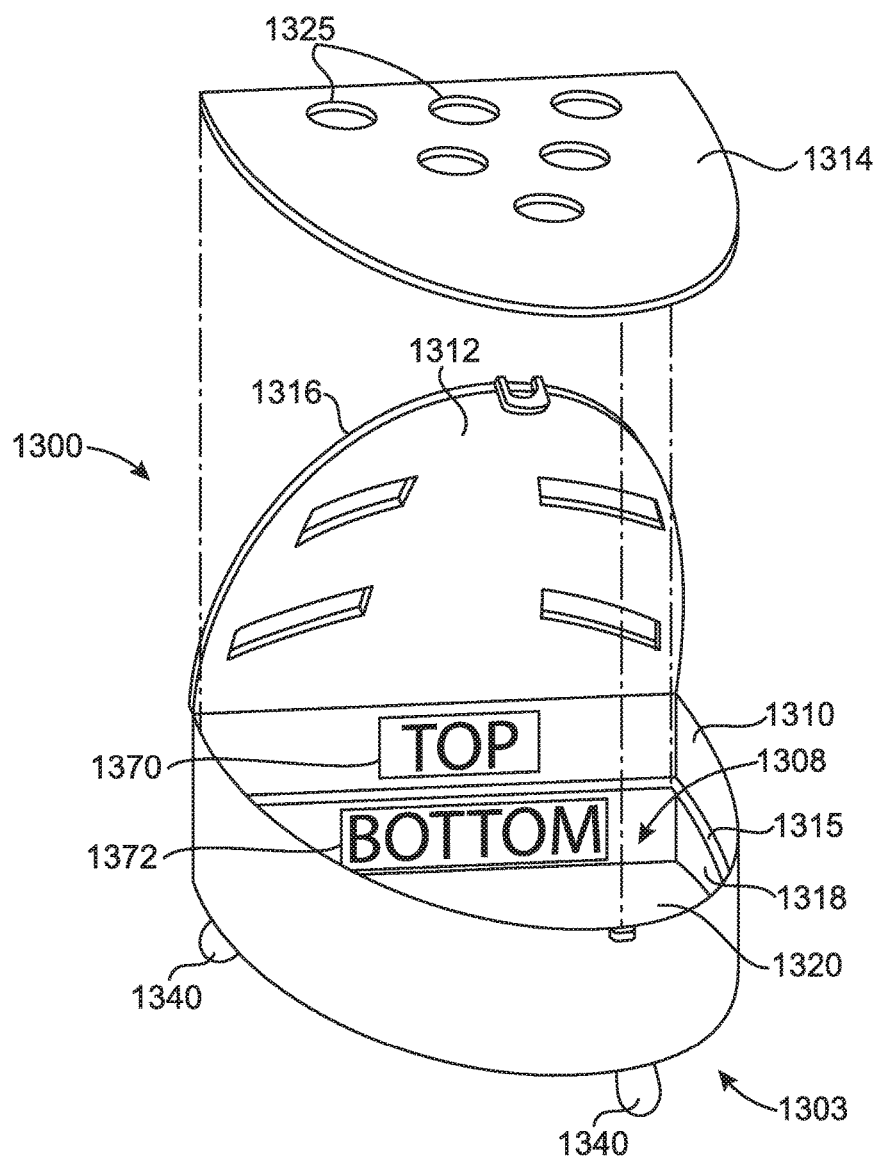
FIG. 15 is an exploded perspective view of the container for dental appliances of FIG. 13.

FIGS. 13-15 show another embodiment of a container 1300 for dental appliances that includes a top portion 1302 and a bottom portion 1303. The container 1300 may include a first compartment 1306 and a second compartment 1308 for storing dental appliances. The first compartment 1306 may be defined by at least one first wall 1310, a first enclosing portion 1312, and a separation plate 1314. The first compartment 1306 may have a first length, first width, and first height configured to accept a first dental appliance. The first wall 1310 may at least partially surround the first compartment 1306, and may be substantially C-shaped to provide a substantially vertical, curved wall around the first compartment. The first wall 1310 may also include portions that are flat or cornered, or other suitable configurations. The first enclosing portion may be included in a door 1316 on the top portion 1302 that may be moveable between a closed position (e.g., FIG. 13) and an open position (e.g., FIG. 14). The first enclosing portion 1312 of the door 1316 may engage with the first wall 1310 when the door is in the closed position and form a ceiling of the first compartment 1306 to retain the dental appliance within the first compartment. In some embodiments, the door 1316 may include a plurality of ports 1324 to allow for fluid circulation into and out of the container 1300. In some embodiments, the door 1316 may have a contoured shape or at least top surface 1304 so as to prevent the container 1300 from resting in a primarily horizontal orientation when placed on the top surface.

The separation plate 1314 may define a floor of the first compartment 1306 upon which a dental appliance may rest when the container 1300 is in an upright orientation. The separation plate 1314 may simultaneously form a ceiling of the second compartment 1308, as best shown in FIG. 15. The second compartment 1308 may be defined by at least one second wall 1318, a second enclosing portion 1320, and the separation plate 1314. The second wall 1318 may at least partially surround the second compartment 1308, and may be substantially C-shaped to provide a substantially vertical, curved wall around the second compartment. The second wall 1318 may also include portions that are flat or have corners, or may include other suitable configurations for surrounding the second compartment. The second enclosing portion 1320 may define a floor of the second compartment 1308 upon which a dental appliance may rest when retained within the second compartment of the container 1300. In some embodiments, ports may be formed through the second enclosing portion 1320 to provide fluid circulation into and out of the second compartment 1308.

FIG. 14 shows an embodiment of the separation plate 1314 in place within the container 1300 and providing separation between the two compartments, while FIG. 15 shows an exploded view of the container with the separation plate removed from the container. As best shown in FIG. 15, outer edges of the separation plate 1314 may rest upon an interior ledge 1315 formed within the container 1300 while the separation plate separates the first compartment 1306 from the second compartment 1308. The interior ledge 1315 may protrude substantially orthogonally from the first and second walls 1310, 1318 toward the interior of the container 1300. In some embodiments, the interior ledge 1315 may surround the entire first and second compartments 1306, 1308, but in other embodiments, the interior ledge may only surround portions of the compartments but enough to support the separation plate 1314. In some embodiments, the separation plate 1314 may instead be hinged along a portion of the first or second walls 1310, 1318 or at a junction between the two, so that the separation plate may pivot upward to provide access to the second compartment 1308. In such embodiments, the separation plate 1314 could also pivot downward and rest against the interior ledge 1315 when in a closed position. In some embodiments, circulation ports 1325 may be formed through the separation plate 1314 to provide additional fluid circulation within the container 1300.

The first and second compartments 1306, 1308 may also include first and second indicators 1370, 1372, respectively, to indicate the upright orientation of the container 1300 and to aid a user in placing the correct dental appliance into each compartment. For example, the embodiment illustrated in FIGS. 14 and 15 includes a first indicator 1370 on the first wall 1310 of the first compartment 1306 that includes the word "TOP" and a second indicator 1372 on the second wall 1318 of the second compartment 1308 that includes the word "BOTTOM." These TOP and BOTTOM indicator labels may indicate that corresponding "top" and "bottom" portions of a dental appliance should be placed in the first and second compartments, 1306, 1308, respectively. For example, some dental appliances, such as retainers or dentures, can a include a distinct top portion for a user's top set of teeth and a distinct bottom portion for the user's bottom set of teeth. The first and second indicators 1370, 1372 corresponding to the first and second compartments 1306, 1308, respectively, provide guidance as to where each distinct top and bottom portion of the dental appliance should be stored. It should be understood that the words TOP and BOTTOM are merely examples of possible first and second indicators, and that other suitable indicators are contemplated herein.

The bottom portion 1303 of the container 1300 may also include feet 1340 that may position the container in a primarily upright, horizontal position, as shown in FIGS. 13-15, when the feet are resting upon a surface, such as a table or counter. It is contemplated herein that any suitable number of feet 1340 for holding the container 1300 in an upright position may be used.

The foregoing description and drawings merely explain and illustrate the invention and the invention is not limited thereto. While the specification is described in relation to certain implementation or embodiments, many details are set forth for the purpose of illustration. Thus, the foregoing merely illustrates the principles of the invention. For example, the invention may have other specific forms without departing from its spirit or essential characteristic. The described arrangements are illustrative and not restrictive. To those skilled in the art, the invention is susceptible to additional implementations or embodiments and certain of these details described in this application may be varied considerably without departing from the basic principles of the invention. It will thus be appreciated that those skilled in the art will be able to devise various arrangements which, although not explicitly described or shown herein, embody the principles of the invention and, thus, within its scope and spirit.

What is claimed is:

1. A container for dental appliances comprising:
   a first compartment defined by at least one first wall, a first enclosing portion, and a separation plate, the first compartment being configured to accept a first dental appliance and being indicated by a first indicator;
   a second compartment defined by at least one second wall, a second enclosing portion, and the separation plate, the second compartment being configured to accept a second dental appliance and being indicated by a second indicator;
   a moveable and closeable door which opens to permit access to at least one of the first compartment and the second compartment;
   wherein each of the first and second indicators are movable between an occupied position and an empty position;
   wherein the separation plate at least partially separates the first compartment from the second compartment; and
   wherein the container comprises a plurality of ports to allow fluid circulation.

2. The container of claim 1 wherein:
   the first indicator is in the occupied position when the first dental appliance is present within the first compartment, and in the empty position when the first compartment is empty; and
   the second indicator is in the occupied position when the second dental appliance is present within the second compartment, and in the empty position when the second compartment is empty.

3. The container of claim 1, wherein the door is in moveable communication with at least one of the first enclosing portion or the second enclosing portion.

4. The container of claim 1, wherein the first compartment and the second compartment are complementary and are separated by the separation plate.

5. The container of claim 4, wherein the separation plate is movable.

6. The container of claim 4, wherein the separation plate comprises ports to allow circulation.

7. The container of claim 1, wherein the container further comprises an orientation indication to indicate an orientation.

8. The container of claim 7, wherein the orientation indication indicates that a first surface of the container is a top of the container.

9. The container of claim 8, wherein a second surface is opposite the first surface and is a bottom of the container.

10. The container of claim 9, wherein the second surface of the container comprises at least one foot.

11. The container of claim 8, wherein the first surface is curved such that the container cannot rest in a primarily horizontal orientation if placed on the first surface.

12. The container of claim 1, wherein the first indication and the second indication are different indications.

13. The container of claim 1, wherein the first compartment is complementary to a first dental device and the second compartment is complementary to a second dental device.

14. The container of claim 1, further comprising a surrounding container which encloses the container.

15. The container of claim 14, wherein the surrounding container does not have circulation openings.

16. The container of claim 1, further comprising a first sensing device.

17. The container of claim 16, wherein the first sensing device is configured to move the first indicator between the empty position and the occupied position.

18. The container of claim 17, further comprising a second sensing device.

19. The container of claim 18, wherein the second sensing device is configured to move the second indicator between the empty position and the occupied position.

20. The container of claim 16, wherein the first sensing device is an electronic sensor.

* * * * *